(12) United States Patent
Allen et al.

(10) Patent No.: US 8,167,930 B2
(45) Date of Patent: May 1, 2012

(54) STENT GRAFT FOR TREATMENT OF EMERGENCY RUPTURE OF A VESSEL

(75) Inventors: Robert James Allen, Garran (AU);
David Ernest Hartley, Wannanup (AU);
Werner D. Ducke, Eight Mile Plains (AU)

(73) Assignees: William A. Cook Australia Pty. Ltd., Queensland (AU); Cook Medical Technologies LLC, Bloomington, IN (US)

( * ) Notice: Subject to any disclaimer, the term of this patent is extended or adjusted under 35 U.S.C. 154(b) by 648 days.

(21) Appl. No.: 11/983,092

(22) Filed: Nov. 7, 2007

(65) Prior Publication Data

US 2008/0147163 A1    Jun. 19, 2008

Related U.S. Application Data

(60) Provisional application No. 60/857,228, filed on Nov. 7, 2006.

(51) Int. Cl.
*A61F 2/06*        (2006.01)
(52) U.S. Cl. ...................................... 623/1.35; 623/1.24

(58) Field of Classification Search ................... 623/1.1, 623/1.35, 1.36, 1.15, 1.16, 1.24, 1.13, 1.34
See application file for complete search history.

(56) References Cited

U.S. PATENT DOCUMENTS

2003/0204243 A1 * 10/2003 Shiu ............................ 623/1.16
2004/0082990 A1 *  4/2004 Hartley ........................ 623/1.13

FOREIGN PATENT DOCUMENTS

| WO | WO 98/53761 | 12/1998 |
| WO | WO 2004/017867 A1 | 3/2004 |
| WO | ISR/PCT/US07/023472 | 3/2008 |
| WO | PCT/US07/023472 | 3/2008 |

* cited by examiner

*Primary Examiner* — Thomas J Sweet
*Assistant Examiner* — Matthew Schall
(74) *Attorney, Agent, or Firm* — Richard J. Godlewski

(57) ABSTRACT

A stent graft (2) for treatment of an emergency rupture of, for instance, the aorta adjacent the aortic bifurcation. The stent graft comprising a tubular body (8) with a bifurcation (10) in the tubular body defining a first long leg (12) and a second short leg (14). The second leg has a valve arrangement (18) to prevent fluid flow through the second leg from the stent graft. The valve can be opened from external of the stent graft for the placement of a leg extension stent graft (90) therethrough.

2 Claims, 7 Drawing Sheets

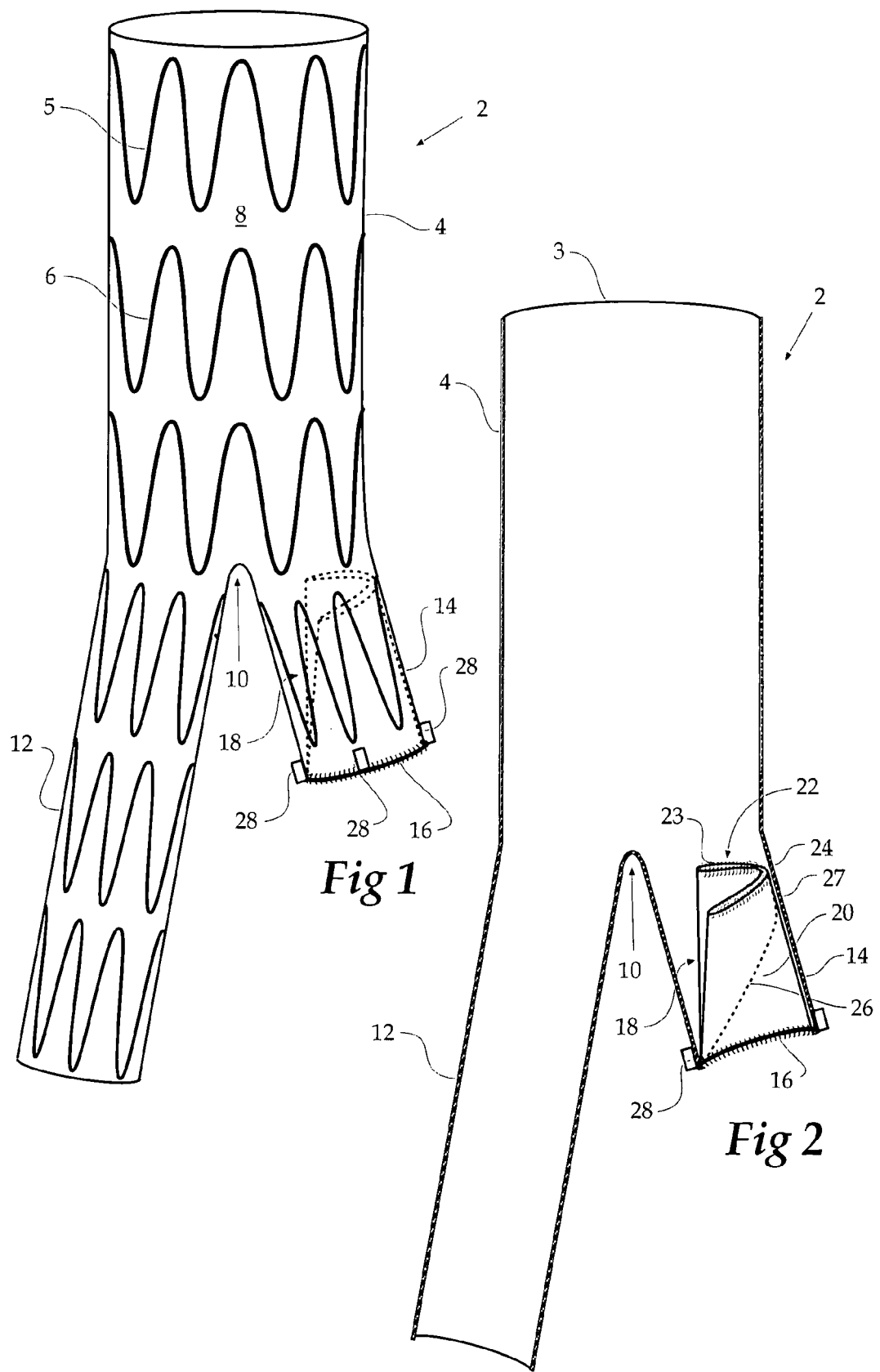

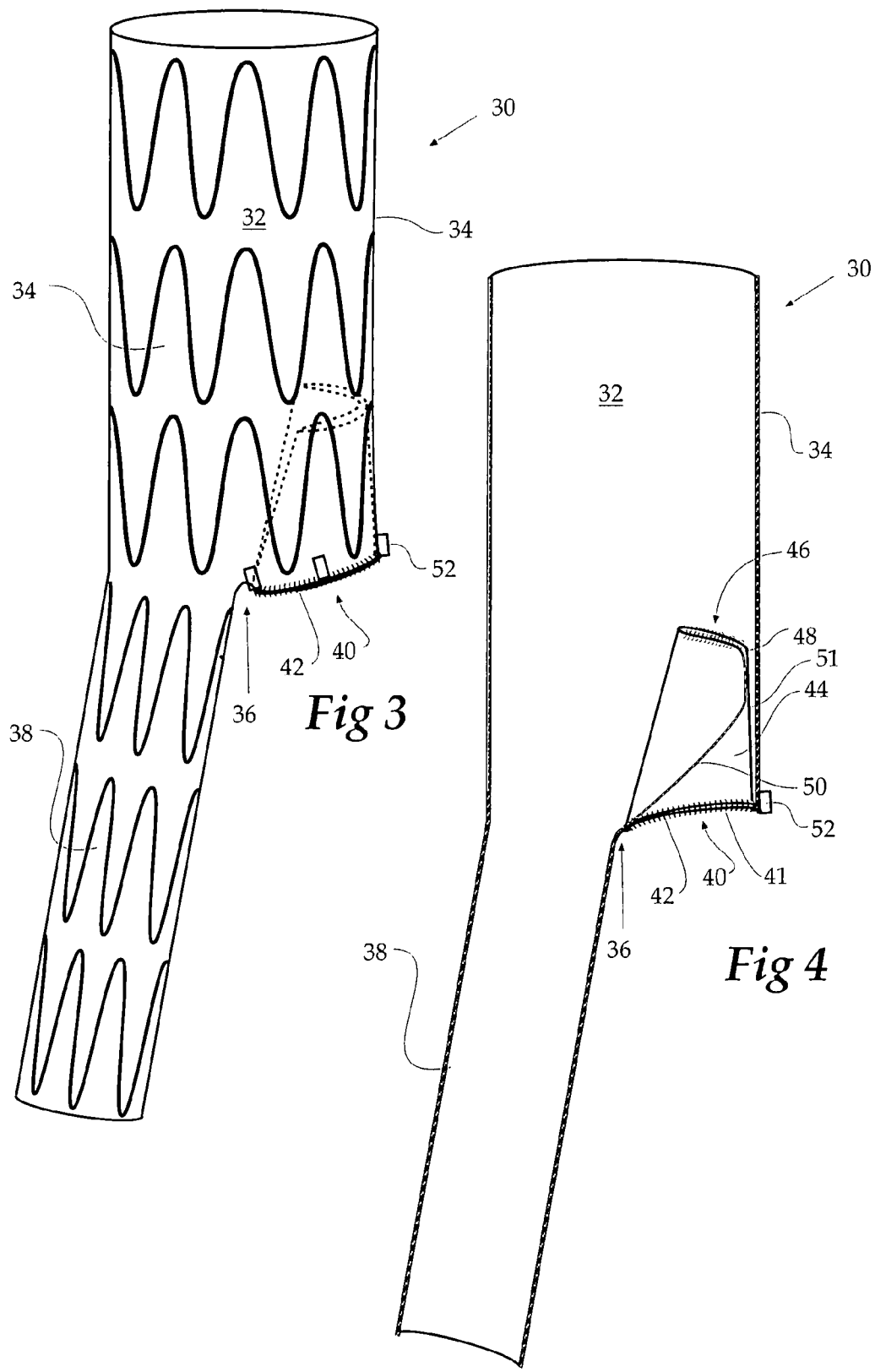

STENT GRAFT FOR TREATMENT OF EMERGENCY RUPTURE OF A VESSEL

CROSS-REFERENCE TO RELATED APPLICATIONS

This application claims priority of provisional application Ser. No. 60/857,228, filed Nov. 7, 2006.

TECHNICAL FIELD

This invention relates to a medical device and more particularly to a medical device suitable treatment of emergency rupture in vessels of the human or animal body.

BACKGROUND OF THE INVENTION

In cases where an artery of the human or animal body has ruptured due to some trauma such as an accident or due to damage of the vessel wall due to stenosis or disease, it is desirable to, as soon as possible, deploy a stent graft across the rupture to isolate the artery wall, in that region, from blood flow in the artery. Where the artery includes a bifurcation such as the aortic bifurcation it is possible to place an aorto-uni-iliac stent graft extending from a portion of the aorta above the rupture into one of the iliac arteries, however, such a procedure does not completely isolate the rupture region because of cross flow of blood in small arteries between the iliac and femoral arteries.

It may be possible to deploy a stent graft with a bifurcation through one of the iliac arteries and then deploy a leg extension stent graft into the other of the other iliac arteries to connect with the bifurcated stent graft, however, this can be a relatively long and more complex procedure and blood loss through the rupture during the procedure can be serious.

It is the object of this invention to provide a stent graft arrangement which will assist in over coming excessive blood loss in the case of an emergency rupture in the case of a vessel incorporating a bifurcation and to provide an option for further treatment or at least providing a useful alternative to a surgeon.

Throughout this specification the term "distal" with respect to a portion of the aorta, a deployment device or a prosthesis means the end of the aorta, deployment device or prosthesis further away in the direction of blood flow away from the heart and the term "proximal" means the portion of the aorta, deployment device or end of the prosthesis nearer to the heart. When applied to other vessels similar terms such as caudal and cranial should be understood.

In our earlier patent application, PCT Patent Publication No. WO 98/53761 entitled "A Prosthesis and a Method Deploying a Prosthesis" there is disclosed an introducer for a stent graft which can be used to deploy the stent graft according to the present invention. This feature and other features disclosed in WO 98/53761 are incorporated herewith in their entirety into this specification.

SUMMARY OF THE INVENTION

In one form thereof, the invention is said to reside in a stent graft for treatment of an emergency rupture of a vessel of the human or animal body which incorporates a vessel bifurcation, the stent graft comprising a main tubular body of a biocompatible graft material defining a main lumen therethrough, a graft bifurcation in the tubular body defining a first long leg extending from the graft bifurcation and either a second short leg extending from the graft bifurcation or an aperture or fenestration, each of the first long leg and second short leg having respective leg lumens therethrough, each leg lumen or aperture being in fluid communication with the main lumen, the second short leg or aperture comprising a valve arrangement to prevent fluid flow through the second short leg or aperture from the main lumen and the valve arrangement being able to be opened from outside of the stent graft for the placement of a leg extension stent graft therethrough.

Preferably, from the graft bifurcation a second short leg is defined and the stent graft can be introduced into the vessel with the longer leg extending into one of the vessels extending from the vessel bifurcation and the shorter leg directed towards the other vessels extending from the vessel bifurcation.

Preferably, the second short leg is fastened to the tubular body within the tubular body at an end remote from the graft bifurcation, and can comprise a reinforcing ring of a shape memory metal at a distal end thereof.

Alternatively, the second short leg can be invaginated within the main tubular body.

Preferably, the valve arrangement comprised in the second short leg with the inner end thereof held in a substantially U-shape by a reinforcement ring being formed from a shape memory material and in a twin U-shape and being able to be opened to a circular shape so that a leg extension stent graft can be deployed through it. The substantially U-shape formed by the reinforcement ring can be stitched to the tubular body of the stent graft.

Alternatively, the leg extension stent graft can be an intraluminal plug.

In an alternative form, the invention comprises a stent graft for treatment of an emergency rupture of an aorta of the human or animal body at or near an aortic bifurcation and the aperture or fenestration is defined. The stent graft comprising a main tubular body of a biocompatible graft material defining a main lumen therethrough, a distal end of the tubular body being of a diameter to be received into and seal in an iliac artery and a proximal end being of a diameter to be received into and seal in the aorta, being the aperture in the tubular body intermediate the ends and directed in use towards the contralateral-iliac artery, the aperture including a valve arrangement to prevent fluid flow out of the aperture from the main lumen and the valve arrangement being able to be opened from outside of the stent graft for the placement of a leg extension stent graft therethrough whereby the stent graft can be introduced into the aorta with the distal end extending into the iliac artery, the proximal end being received in the aorta proximally of the rupture and the aperture directed towards the contralateral-iliac artery.

Preferably, the aperture comprises a reinforcing ring of a shape memory metal.

Preferably, the valve arrangement comprises a tube of biocompatible graft material fastened around the aperture and extending into the tubular body with the inner end thereof held in a substantially U-shape by a reinforcement ring being formed from a shape memory material and in a twin U-shape and being able to be opened to a circular shape to deploy a leg extension stent graft therein. The substantially U-shape reinforcement ring can be stitched to the tubular body of the stent graft.

Alternatively, the leg extension stent graft can be an intraluminal plug.

In an alternative form, the invention is said to reside in a stent graft for treatment of an emergency rupture of the aorta adjacent the aortic bifurcation and a second short leg, emerging from the graft bifurcation is defined. The stent graft comprising a main tubular body of a biocompatible graft material defining a main lumen therethrough, a bifurcation in the tubular body defining a first long leg and the second short leg, each of the first and second legs having respective lumens therethrough and each in fluid communication with the main lumen, the second short leg comprising a valve arrangement to prevent fluid flow through the second short leg from the main lumen and the valve arrangement being able to be opened from outside of the stent graft for the placement of a leg extension stent graft therethrough. The second short leg having a distal opening and the valve arrangement comprising a tube of biocompatible material fastened around the distal opening and extending back into the second short leg.

Preferably, the tube of biocompatible material is fastened to the tubular body at an end remote from its attachment to the second short leg.

Preferably, the valve arrangement comprises a reinforcement ring on the tube at an end remote from its attachment to the second short leg, the reinforcement ring being formed from a shape memory material and in a twin U-shape and being able to be opened to a circular shape so that a leg extension stent graft can be deployed through it.

Preferably, the second short leg comprises a reinforcing ring of a shape memory metal at a distal end thereof.

Alternatively, the second short leg can be invaginated within the main tubular body.

Preferably, the valve arrangement comprised in the second short leg with the inner end thereof held in a substantially U-shape by a reinforcement ring being formed from a shape memory material and in a twin U-shape and being able to be opened to a circular shape. The substantially U-shape by a reinforcement ring can be stitched to the tubular body of the stent graft.

Preferably, the valve arrangement comprises a tube of biocompatible material fastened to the second short leg and extending back into the second short leg with a closure arrangement associated with the tube of biocompatible material and the closure arrangement resiliently closing off the tube of biocompatible material.

Alternative, the valve arrangement can comprise an aperture or a fenestration adjacent the junction between the main body instead of the second short leg.

It will be seen that by this invention there is provided an arrangement which initially is essentially an aorto-uni-iliac stent graft, that is, it has a main body portion to be deployed into the aorta, for instance, proximal of the aortic bifurcation and a single leg which can be placed into one of the iliac arteries but that it also has an aperture with a valve arrangement and the valve arrangement being able to be opened from outside of the stent graft for the placement of a leg extension stent graft therethrough. Such a device can be deployed by known endovascular techniques via a femoral and iliac artery. Such deployment will assist in stabilising a patient until a surgeon can decide whether to deploy a leg extension stent graft through the contralateral iliac artery into the valve arrangement or to deploy a plug into the contra-iliac artery and perform a femoro-femoral crossover graft operation.

The valve arrangement according to this invention is kept closed by the twin U shape and sealed by the walls of the tube engaging against each other by aortic blood pressure until such time as the valve arrangement is opened from outside of the stent graft.

BRIEF DESCRIPTION OF THE DRAWING

This then generally describes the invention but to assist with understanding reference will now be made to the accompanying drawings that show preferred embodiments of the invention.

In the drawings:

FIG. 1 shows a first embodiment of stent graft according to the present invention;

FIG. 2 shows a cross sectional view of the stent graft shown in FIG. 1;

FIG. 3 shows an alternative embodiment of stent graft according to the present invention;

FIG. 4 shows a cross-sectional view of the embodiment of stent graft shown in FIG. 3;

DETAILED DESCRIPTION

Figure 5:
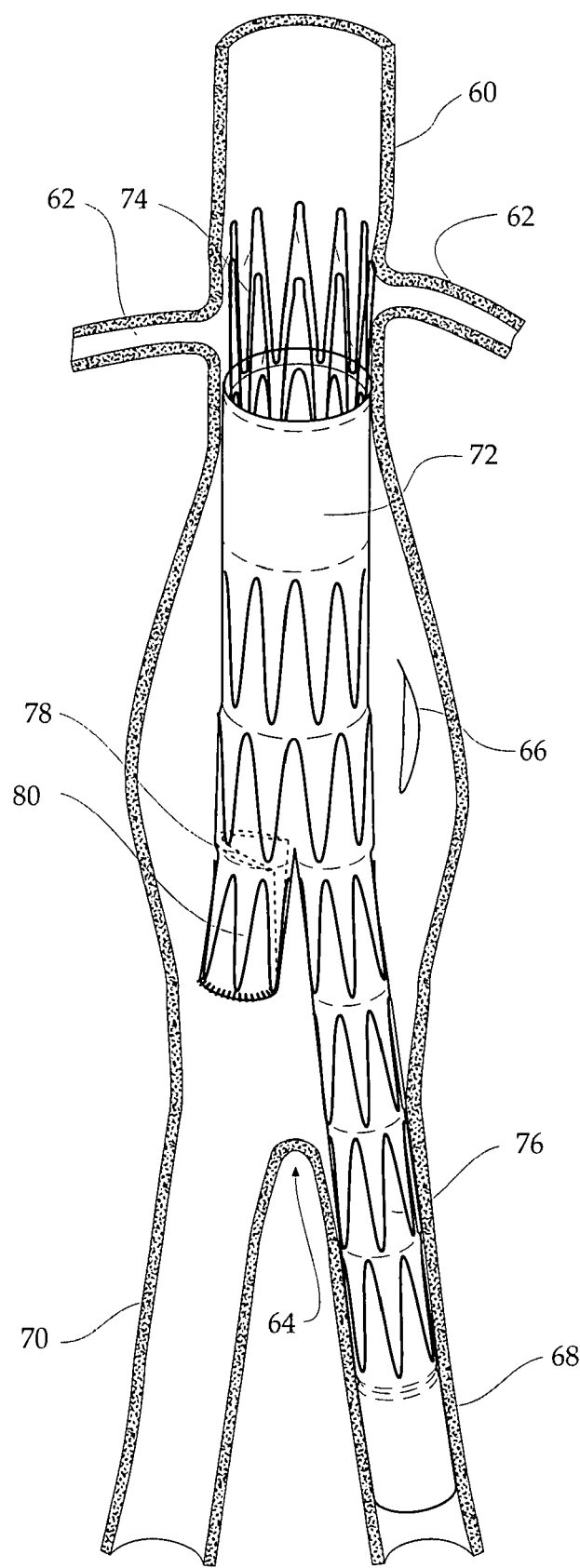
FIG. 5 shows a schematic aorta of a patient with the embodiment of the stent graft as shown in FIG. 1 deployed therein.

FIG. 1 and FIG. 2 show a first embodiment of stent graft according to the present invention. FIG. 1 shows a perspective view and FIG. 2 shows a longitudinal cross sectional view of the stent graft of FIG. 1. In this embodiment the stent graft 2 comprises a tubular wall 4 of a biocompatible material supported by stents 6. The actual number and placement of stents may vary depending upon the size of the stent graft and its intended configuration within the human or animal body. The stent graft has a main tubular body 8 and a bifurcation 10 from which extends a long tubular leg 12 and a short tubular leg 14.

The stent graft 2 may have an exposed stent (not shown) extending proximally from the proximal end 3 to assist with fixation or can have barbs extending from the proximal-most stent 5.

The main tubular body can have an expanded diameter of from 25 to 45 mm and a length of from 100 to 250 mm and each of the first and second legs can have a diameter of from 10 to 20 mm. The first leg can have a length of from 50 to 150 mm and the second leg can have a length of from 20 to 50 mm.

The short leg 14 terminates in a ring reinforcement 16 and a valve arrangement 18 extending back into the short leg from the ring reinforcement 16.

The valve arrangement 18 comprises a tube of biocompatible graft material 20 which extends back into the short leg 14 and at its proximal end 22 there is a twin U-shaped reinforcing ring 24. The twin U-shaped reinforcing ring 24 is essentially a continuous ring of shape memory metal such as Nitinol which, when folded back into itself, forms the twin U-shape with one U shape being inside the other. The reinforcing ring 24 is stitched to the proximal end of the tube 20 by stitching 23. The twin U-shape of the reinforcing ring causes the tube 20 to fold in halves and in effect the combination of the twin U-shape and the folded tube acts as a valve to prevent fluid flow through the short leg 14. The fluid flow is prevented by the flap 26 of the tube 20 bearing against the part 27 of the tube 20 and the inner wall of the short leg 14. The length of the tube 20 can be 20 to 40 mm and it can have a diameter of from 10 to 20 mm.

Radiopaque markers 28 are provided around the distal end of the short leg 14 to assist catheterisation of the short leg once the stent graft has been deployed.

FIGS. 3 and 4 show an alternative embodiment of stent graft according to the present invention. FIG. 3 shows a perspective view and FIG. 4 shows a longitudinal cross sectional view of the stent graft of FIG. 3. In this embodiment the stent graft 30 includes a main tubular body 32 defined by a tubular wall 34 extending to a bifurcation or branch 36. From the bifurcation or branch 36 a long tubular leg 38 extends and also there is an aperture or fenestration 40 which is defined by a reinforcing ring 42 substantially at the junction between the main tubular body and the long leg.

Extending back into the main tubular body 32 is a tube 44 of biocompatible material which is stitched to the main tube around the periphery of the aperture 40 by stitching 45. At its proximal end 46 the tube 44 has a reinforcing ring 48 of a shape memory metal such as Nitinol retained by stitching 47. The reinforcing ring 48 is a continuous length of the shape memory metal formed into a pair of U-shapes with one U shape being inside the other and thereby normally holding one side wall of the tube 44 against the other. This in effect closes off the tube 44 by means of a flap 50 which is one of the walls of the tube engaging against the side 51 of the tube 44 to form a valve to prevent fluid flow from the tubular body 32 out through the aperture 40. The aperture 40 is surrounded by radiopaque markers 52 to assist a surgeon in locating the aperture for catheterisation.

The main tubular body can have an expanded diameter of from 25 to 45 mm and a length of from 100 to 250 mm and the first leg can have a diameter of from 10 to 20 mm. The first leg can have a length of from 50 to 150 mm. The length of the tube 44 can be 20 to 40 mm and it can have a diameter when opened out of from 10 to 20 mm.

FIG. 5 shows a schematic aorta 60 of a human body. The aorta has renal arteries 62 and lower down an aortic bifurcation 64. Extending from the aortic bifurcation are iliac arteries 68 and 70.

A rupture 66 has occurred in the aorta and it is the intention of a physician to isolate the rupture by placement of a stent graft into the aorta to span the rupture.

A stent graft 72 of the type shown in FIGS. 1 and 2 has been deployed so that its proximal end is adjacent to the renal artery 62 with an infra-renal exposed stent 74 assisting and supporting the proximal end of the stent graft. The long leg 76 extends down the iliac artery 68 and seals therein. The valve arrangement 78 in the short leg 80 of the stent graft 72 prevents blood flow from the aorta into the aorta in the region of the aortic bifurcation and the contralateral iliac artery 70.

To deploy the stent graft 72 of the present invention the Seldinger technique is used via a femoral artery and iliac artery into the aorta and the stent graft is carried on a deployment device.

There is a certain amount of blood flow possible between the iliac arteries through smaller vessels between them downstream of the aortic bifurcation and hence the arrangement shown in FIG. 5 does not completely isolate the rupture 66.

The placement of the stent graft as shown in FIG. 5 does, however, give the physician time to decide what method can be used to isolate the rupture.

Figure 6:
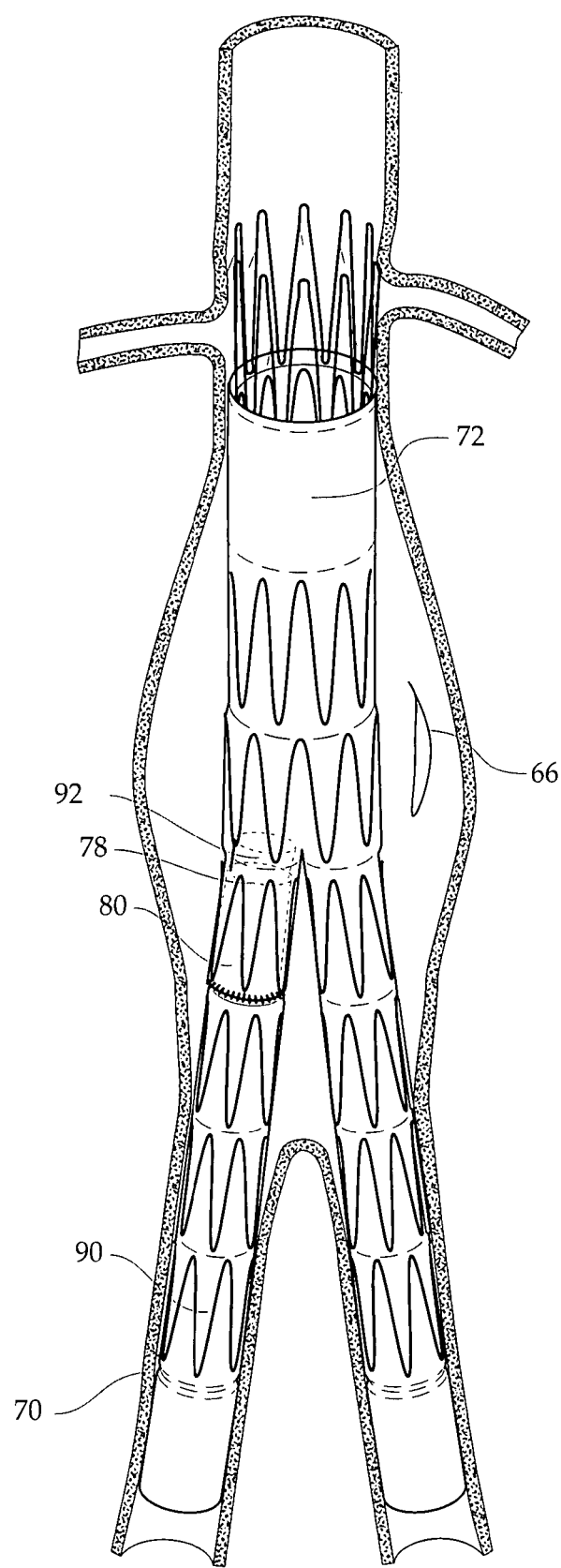
FIG. 6 shows a further stage of the process depicted in FIG. 5 with a leg extension stent graft deployed through the valve arrangement.

In FIG. 6 one such method is depicted. In this embodiment a leg extension stent graft 90 has been placed through the contra lateral iliac artery 70 into the short leg 80 to open the valve arrangement 78. The proximal end 92 of the leg extension stent graft 90 passes up into the main body of the stent graft 72 and the distal end of the leg extension stent graft 90 seals into and undamaged portion of the contra lateral iliac artery 70.

By this arrangement the rupture 66 is isolated. To deploy the leg extension stent graft again the Seldinger technique can be used via the contralateral iliac artery.

Figure 7:
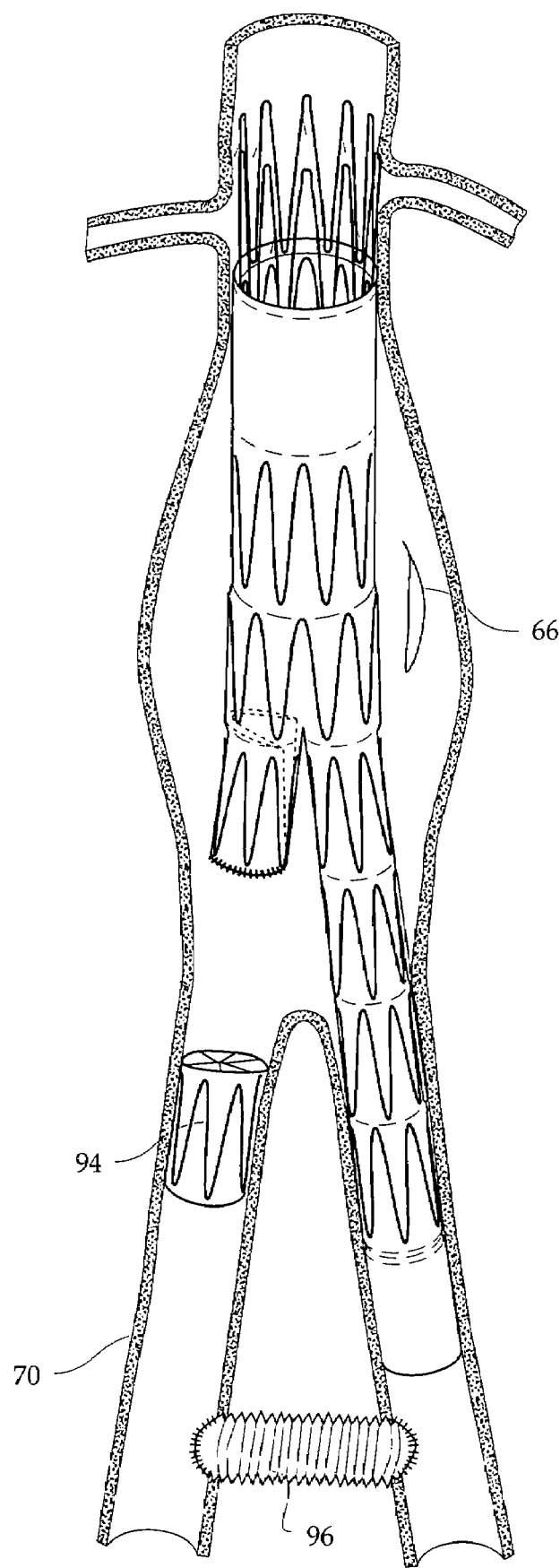
FIG. 7 shows an alternative subsequent step to that shown in FIG. 5.
Figure 8:
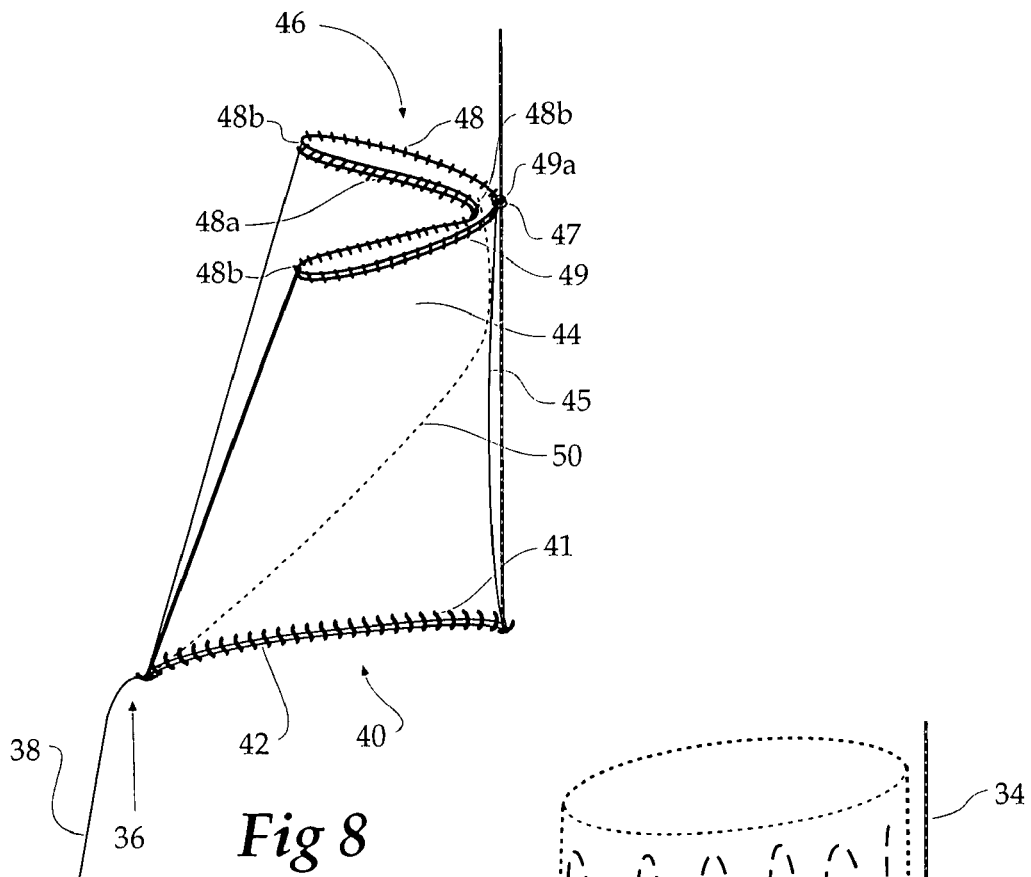
FIG. 8 shows detail of the valve arrangement for the embodiment shown in FIG. 3.

An alternative arrangement is shown in FIG. 7.

In this embodiment for some reason perhaps because of an advanced stenosis or the like it is not possible to deploy a full leg extension stent graft through the contra iliac artery 70.

Instead the physician has deployed an intraluminal plug 94 and performed a femoro-femoral cross-over grafting operation using a piece of corrugated graft material 96. Once again by this arrangement the area of the rupture 66 has been isolated. To deploy the intraluminal plug again the Seldinger technique can be used via the contralateral iliac artery but because it is a much smaller component it may be deployed through the stenosed arteries.

FIGS. 8 to 11 show detail of a stent graft incorporating a valve side arm according to the stent graft illustrated in FIGS. 3 and 4. The same reference numerals will be used in FIGS. 8 to 11 for corresponding items.

The valve arrangement includes an aperture or fenestration 40 in the distal end of the tubular body 34 with a tube of a biocompatible graft material 44 extending into the stent graft. The aperture 40 has a reinforcing ring 42 of a shape memory metal such as Nitinol or similar wire stitched around the aperture by means of stitching 41. At the proximal end of the tube 44 is a twin U-shaped reinforcing ring 48 which is stitched to the tube 44 by stitching 49. The twin U-shape is formed from a continuous length of shape memory metal with one U-shape within the other. The bends 48b between the outer U-shape 49 and the inner U-shape 48a are such that the outer U-shape is slightly less length than half of the full circumference of the reinforcement ring. The reinforcing ring 48 is formed into its twin U-shape and it being a shape memory metal is retained in that shape. The twin U-shape causes a flap 50 of the tube 44 to engage against the other wall 45 of the tube 44 as well as both engaging against the inside of the wall 34 of the stent graft thereby closing off blood flow from inside the stent graft out through the aperture 40.

It will be noted that the apex 49a of the outer of the U-shaped reinforcement 49 is stitched to the wall 34 of the stent graft by stitching 47 to hold it in its desired position. Also the inner portion 48a of the twin U-shaped ring reinforcement 48 at its apex is slightly lower than the apex 49a of outer portion 49 of the twin U-shaped ring reinforcement 48. This assists in ensuring that the flap 50 engages with the inside of the wall 54.

Figure 9:
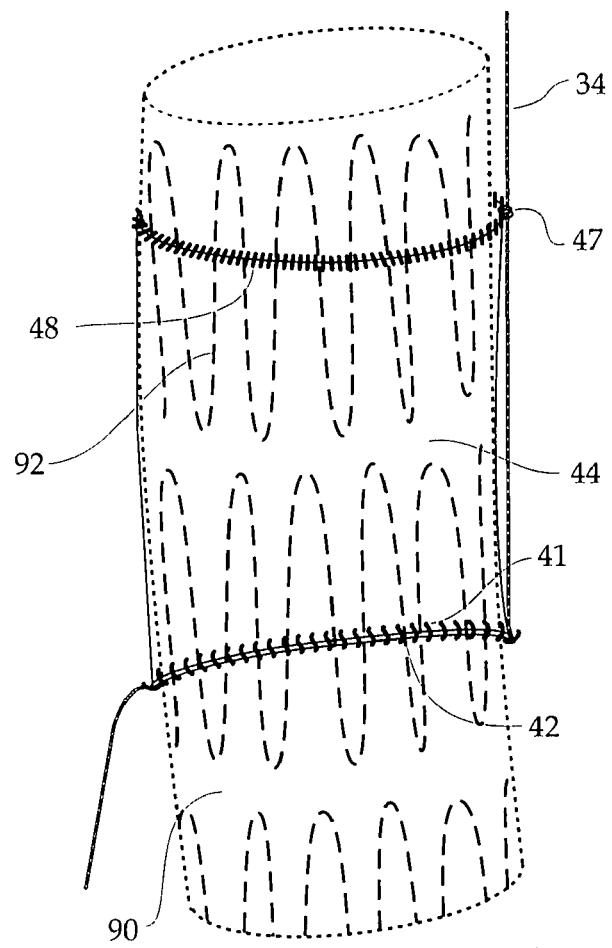
FIG. 9 shows the embodiment of FIG. 8 with a leg extension stent graft deployed through the valve arrangement.
Figure 10:
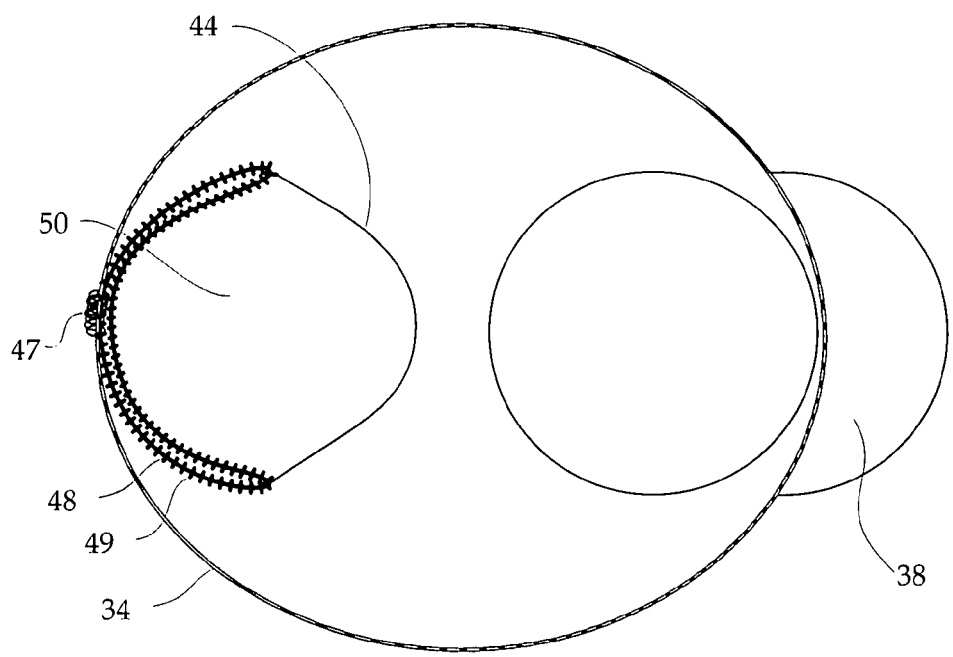
FIG. 10 shows a transverse cross section of the embodiment shown in FIG. 3 particularly showing the configuration of the valve arrangement.
Figure 11:
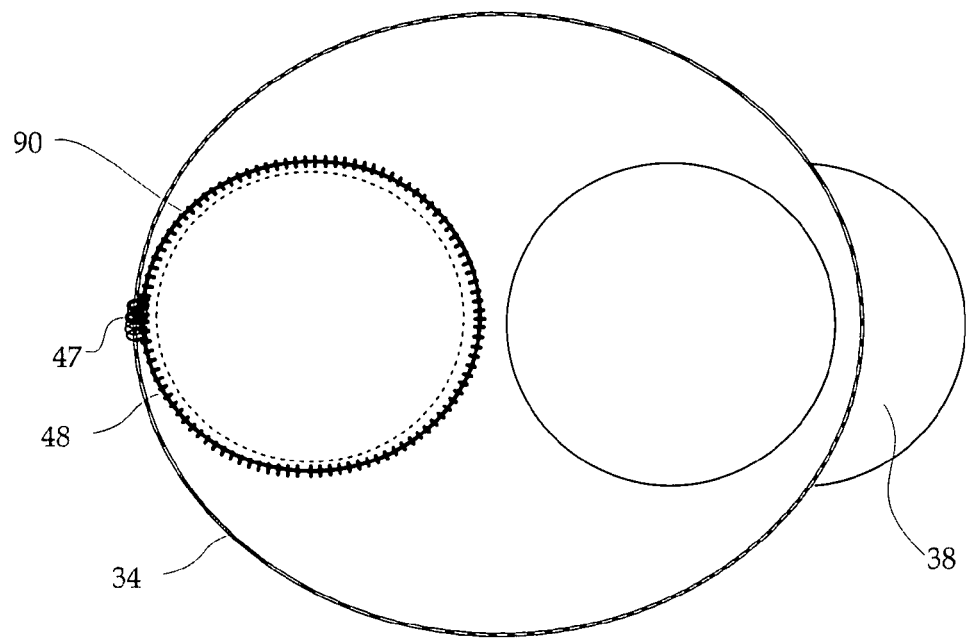
FIG. 11 shows the embodiment in FIG. 10 after a leg extension stent graft has been deployed into the valve arrangement.

If, however, the aperture 40 is catheterised from externally via the contralateral iliac artery the flap 50 can be lifted and the twin U-shape can be opened out to the form shown in FIGS. 9 and 11. A leg extension stent graft 90 can then be deployed through the aperture. Self expanding or balloon expandable stents 92 on the leg extension stent graft 90 will open and hold open the twin U shape into a circular shape.

Throughout this specification various forms of the invention are discussed but the invention is not limited to any one of these but may reside in two or more combined together. The examples are given for illustration and not for limitation.

What is claimed is:

1. An emergency rupture stent graft for treatment of a vessel of the human or animal body which incorporates a vessel bifurcation, the stent graft comprising a main tubular body of a biocompatible graft material defining a main lumen therethrough, a graft bifurcation in the tubular body defining a first long leg extending from the graft bifurcation and a second short leg extending from the graft bifurcation, each of the long leg and the short leg comprising a biocompatible graft material and defining respective leg lumens therethrough, each leg lumen being in fluid communication with the main lumen, the second short leg being invaginated within the main tubular body and being fastened to the tubular body within the tubular body at an end remote from the graft bifurcation, the second short leg comprising a proximal end remote from the graft bifurcation and a distal end adjacent to the graft bifurcation, the second short leg comprising a circular continuous ring of shape memory metal being stitched to the second short leg at the distal end whereby to keep open the distal end of the second short leg, the second short leg comprising a valve arrangement to prevent fluid flow through the second short leg from the main lumen and the valve arrangement being able to be opened from outside of the stent graft for the placement of a leg extension stent graft therethrough, the valve arrangement comprising a continuous ring of shape memory metal being stitched to the second short leg at the proximal end thereof, the continuous ring comprising a twin U-shape comprising an inner U-shape and an outer U-shape, the inner U-shape being inside the outer U-shape, each U-shape comprising an apex and the apex of the inner U-shape being more distal than the apex of the outer U-shape, the second short leg thereby forming a inner U-flap and an outer U-flap with the inner U-flap engaging the outer U-flap to provide the valve arrangement, the valve arrangement being able to be opened to a circular shape.

2. The stent graft as in claim 1 wherein the first long leg comprises a diameter to be received into and seal in an iliac artery and the tubular body comprises a proximal end and a distal end, the proximal end being of a diameter to be received into and seal in the aorta, and in use the second short leg being directed towards the contralateral-iliac artery, the valve arrangement preventing fluid flow out of the second short leg from the main lumen and the valve arrangement being able to be opened from outside of the stent graft for the placement of a leg extension stent graft therethrough whereby the stent graft is introduced into the aorta with the distal end extending into the iliac artery, the proximal end being received in the aorta proximally of the rupture and the second short leg directed towards the contralateral-iliac artery.

\* \* \* \* \*